United States Patent [19]
Fassuliotis et al.

[11] Patent Number: 5,980,507
[45] Date of Patent: Nov. 9, 1999

[54] CATHETER COT

[76] Inventors: Thomas M. Fassuliotis; Ginger E. Lowery, both of 4085 Cochran Rd., Gainesville, Ga. 30506

[21] Appl. No.: 09/070,118

[22] Filed: Apr. 30, 1998

[51] Int. Cl.$^6$ ................. A61M 1/00; A61F 5/44
[52] U.S. Cl. ............... 604/540; 604/544; 604/351; 604/358
[58] Field of Search .................. 604/349–352, 604/329, 174, 179, 358, 180, 540, 544; 128/DIG. 26

[56] References Cited

U.S. PATENT DOCUMENTS

| | | | |
|---|---|---|---|
| 1,661,494 | 3/1928 | Nielsen | 604/174 |
| 4,416,664 | 11/1983 | Womack | 604/174 |
| 4,419,097 | 12/1983 | Rowland | 604/352 |
| 4,769,020 | 9/1988 | Eaton | 604/352 |
| 4,820,289 | 4/1989 | Coury et al. | 604/349 |
| 4,865,595 | 9/1989 | Heyden | 604/352 |
| 5,417,668 | 5/1995 | Setzer et al. | 604/263 |
| 5,460,606 | 10/1995 | Daneshvar | 604/174 |
| 5,582,599 | 12/1996 | Daneshvar | 604/263 |
| 5,665,073 | 9/1997 | Bulow et al. | 604/263 |
| 5,667,068 | 9/1997 | Weaver | 206/363 |

*Primary Examiner*—Mark O. Polutta
*Attorney, Agent, or Firm*—Henderson & Sturm

[57] ABSTRACT

A catheter cot 10 and method for collecting urine that has leaked around the periphery of an inflatable balloon 102 on a catheter tube 100 in a patient's urinary tract 200. The catheter cot 10 includes a layer of absorbent material 25 that is wrapped around the periphery of the intermediate portion 105 of the catheter tube 100 and secured thereto by a plurality of adhesive strips 30.

1 Claim, 1 Drawing Sheet

CATHETER COT

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of medical accessories in general, and in particular to a catheter cot for absorbing urine leakage in the vicinity of a catheter.

2. Description of Related Art

As can be seen by reference to the following U.S. Pat. Nos. 5,417,668; 5,582,599; 5,665,073; and 5,667,068, the prior art is replete with myriad and diverse protective cover devices, including protective covers for catheters and the like.

While all of the aforementioned prior art constructions are more than adequate for the basic purpose and function for which they have been specifically designed, they are uniformly deficient with respect to their failure to provide a simple, efficient, and practical device for absorbing urine that leaks from around the edges of an indwelling urinary catheter.

As most health care professionals are no doubt aware, indwelling urinary catheters have an unpleasant side effect in that they are prone to leakage and normally require the use of diapers, plus frequent changes of bed linens and frequent patient baths not to mention the personal discomfort and skin irritation that is experienced by the patient's themselves.

As a consequence of the foregoing situation, there has existed a longstanding need for a new and improved catheter cot that will capture and absorb the leakage from the indwelling urinary catheter to minimize and/or eliminate the aforementioned undesirable side effects, and the provision of such a construction is a stated objective of the present invention.

BRIEF SUMMARY OF THE INVENTION

Briefly stated, the catheter cot that forms the basis of the present invention comprises an absorbent pad unit and a securing unit operatively associated with the absorbent pad unit and adapted to releasably secure the absorbent pad unit in a surrounding relationship to a catheter tube having one end disposed within a male or female patient's urinary tract.

As will be explained in greater detail further on in the specification, the absorbent pad unit comprises a tapered absorbent pad member including a layer of absorbent material and a layer of waterproof material that may be wrapped around a portion of the catheter tube in a funnel fashion.

In addition, the securing unit comprises a plurality of adhesive strips that are operatively associated with both the absorbent pad member and the catheter tube for fixedly securing the catheter cot to the catheter tube to collect and absorb urine.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figures 1, 2:
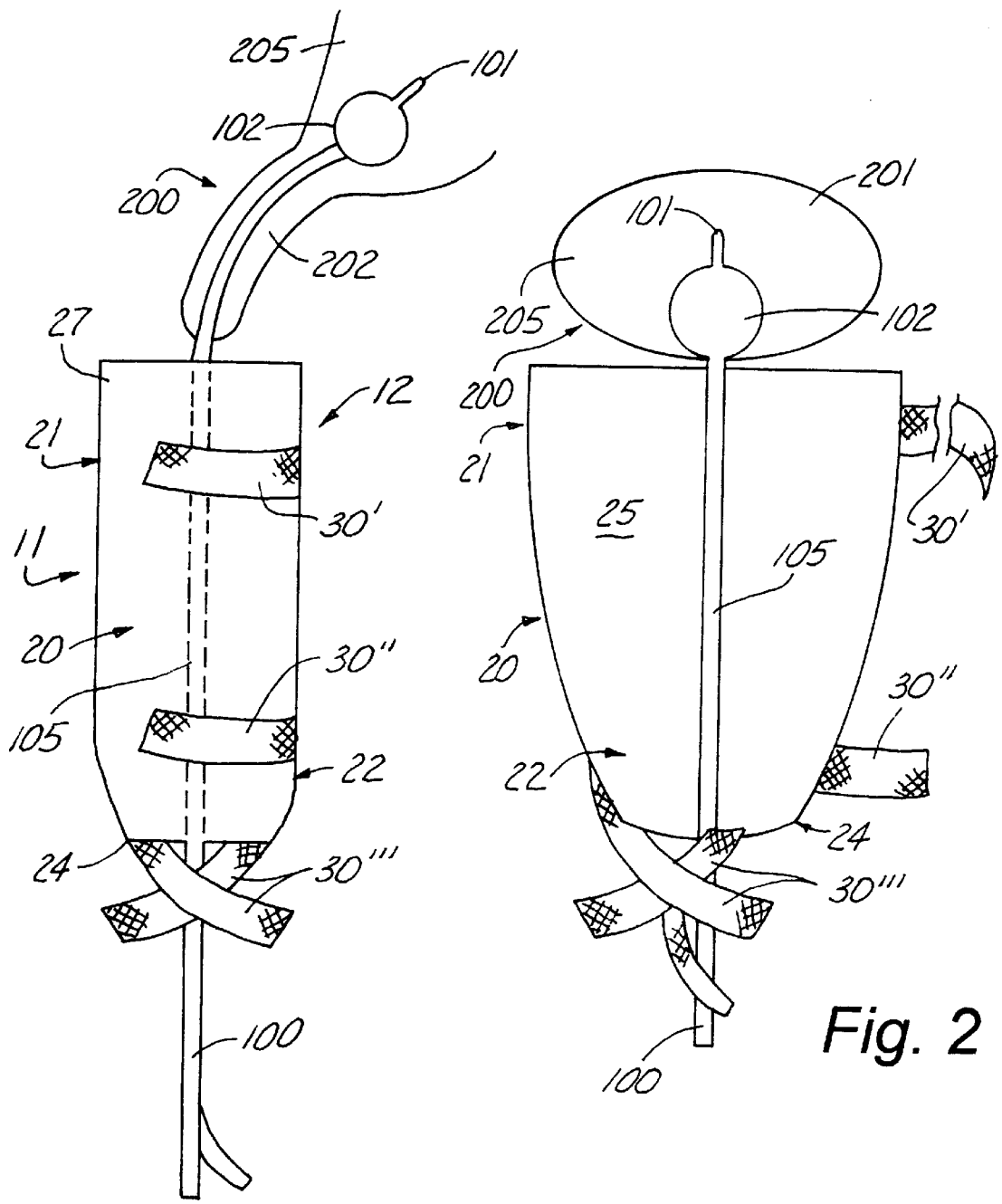
FIG. 1 is a schematic diagram of the catheter cot in the closed position and surrounding a catheter tube having one end disposed in a male urinary tract.
FIG. 2 is a schematic view of the catheter cot in the open position and prior to engaging a catheter tube having one end disposed in a female urinary tract.

As can be seen by reference to the drawings, and in particularly to FIG. 1, the catheter cot that forms the basis of the present invention is designated generally by the reference number 10. The catheter cot 10 comprises in general, an absorbent pad unit 11, and a securing unit 12. These units will now be described in seriatim fashion.

Prior to embarking on a detailed description of the catheter cot 10, it would first be advisable to describe the environment in which the catheter cot is designed to function within. As shown in FIGS. 1 and 2, the catheter cot 10 is designed to be used in conjunction with a catheter tube 100 having one end 101 equipped with a catheter balloon 102 which is deflated to be inserted into a patient's urinary tact 200 by inserting the upper end 101 of the catheter tube 100 through a female's vagina 201 or a male's penis 202 and into the male or female's bladder 205 wherein the balloon 102 is the inflated to form a seal within the patient's urinary tract 200.

As can also be seen by reference to FIGS. 1 and 2, the absorbent pad unit 11 comprises an absorbent pad member 20 having an enlarged upper portion 21 and a tapered lower portion 22. The absorbent pad member 20 is preferably fabricated from an inner layer 25 of non-woven absorbent sterile material and which is also provided with an outer layer 27 of water impervious material such as plastic or the like to confine any collected liquid within the inner absorbent layer 25.

As can also be seen by reference to FIGS. 1 and 2, the securing unit 12 comprises a plurality of strips of adhesive tape 30 that are disposed on both the upper portion 21, the lower portion 22, and the bottom 24 of the absorbent pad member 20.

As shown in the drawings, the tapered configuration of the absorbent pad member 20 allows the absorbent pad member 20 to encircle and surround the intermediate portion 105 of the catheter tube 100. The upper portion 21 of the absorbent pad member 20 can be disposed in a relatively loose frictional engagement with the intermediate portion 105 of the catheter tube 100 via the action of the upper adhesive strip 30', the lower portion 22 of the absorbent pad member 20 can be disposed in a relatively tight frictional engagement with the intermediate portion of the catheter tube 105 via the adhesive strip 30". The bottom 24 of the absorbent pad member 20 can be fixedly secured to the catheter tube 100 by the adhesive strips 30'". The bottom 24 of the absorbent pad member 20 can be fixedly secured to the catheter tube 100 by the adhesive strips 30'" to prevent the catheter cot 10 from sliding downwardly relative to the catheter tube 100.

In this manner, the absorbent pad member 20 can be secured by the adhesive strips 30 in a captive engagement with the catheter tube 100 in close proximity to the patient's urinary tract outlet to collect any urine that has managed to pass between the balloon 102 and the walls of the urinary tract. The generally funnel shaped absorbent pad member 20 will collect and absorb the urine.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

We claim:

1. A catheter cot and catheter tube for the collection of urine that passes between the walls of a patient's urinary tract and an inflatable balloon) disposed on the upper portion of the catheter tube wherein the catheter tube has a lower portion adapted to extend outside of the patient's urinary tract and wherein the catheter cot comprises:

an absorbent pad member having an enlarged upper end and a tapered lower end and including a layer of absorbent material having one side provided with a layer of waterproof material;

a first plurality of adhesive strips having opposite ends wherein both of the opposite ends are connected to the layer of waterproof material for frictionally engaging the absorbent pad member to the lower portion of the catheter tube; and, a second plurality of adhesive strips on a bottom portion having opposite ends wherein one of the ends are connected directly to the layer of waterproof material and the other of the ends are connected directly to the lower portion of the catheter tube.

\* \* \* \* \*